(12) United States Patent
Färber et al.

(10) Patent No.: US 7,713,984 B2
(45) Date of Patent: May 11, 2010

(54) PHARMACEUTICAL USES

(75) Inventors: Lothar Färber, Heroldsberg (DE); Wolfgang Mueller, Im Rehwechsel 30, 4102 Binningen (CH); Thomas Stratz, Purkersdorferstrasse 51, D-79713 Bad Säckingen (DE)

(73) Assignees: Novartis AG, Basel (CH); Wolfgang Mueller, Binningen (CH); Thomas Stratz, Bad Sackingen (DE)

( * ) Notice: Subject to any disclaimer, the term of this patent is extended or adjusted under 35 U.S.C. 154(b) by 0 days.

(21) Appl. No.: 12/008,777

(22) Filed: Jan. 14, 2008

(65) Prior Publication Data

US 2008/0161329 A1 Jul. 3, 2008

Related U.S. Application Data

(63) Continuation of application No. 11/715,805, filed on Mar. 8, 2007, now abandoned, which is a continuation of application No. 10/947,967, filed on Sep. 23, 2004, now abandoned, which is a continuation of application No. 10/222,060, filed on Aug. 16, 2002, now abandoned, which is a continuation of application No. 09/792,801, filed on Feb. 23, 2001, now abandoned, which is a continuation of application No. PCT/EP99/06215, filed on Aug. 24, 1999.

(30) Foreign Application Priority Data

Aug. 25, 1998 (GB) ................................. 9818467.4
Dec. 4, 1998 (GB) ................................. 9826692.7

(51) Int. Cl.
*A61K 31/517* (2006.01)
*A61K 31/4706* (2006.01)
*A61K 31/473* (2006.01)
*A61K 31/4468* (2006.01)

(52) U.S. Cl. .................. 514/266.22; 514/307; 514/311; 514/318; 514/319

(58) Field of Classification Search ........................ None
See application file for complete search history.

(56) References Cited

U.S. PATENT DOCUMENTS

| 5,310,743 | A |   | 5/1994  | Schilling et al. ............ 514/311 |
| 5,604,247 | A |   | 2/1997  | Von Sprecher et al. ...... 514/320 |
| 5,891,875 | A |   | 4/1999  | Hipskind et al. .......... 514/235.2 |
| 5,945,106 | A | * | 8/1999  | Sinnott ....................... 424/774 |
| 5,965,562 | A |   | 10/1999 | Ofner et al. ................... 514/259 |
| 6,020,346 | A |   | 2/2000  | Armour et al. ............... 514/326 |

FOREIGN PATENT DOCUMENTS

| EP | 532 456     | 3/1993  |
| EP | 707 006     | 4/1996  |
| EP | 739 892     | 10/1996 |
| WO | WO 9624353  | 8/1996  |
| WO | 97/24324    | 7/1997  |
| WO | WO 9733581  | 9/1997  |
| WO | WO 9738692  | 10/1997 |
| WO | 98/24438    | 6/1998  |
| WO | WO99/17609  | * 4/1999 |

OTHER PUBLICATIONS

Wallace D.J., Annals of Medicine, "The Fibromyalgia Syndrome", vol. 29, No. 1, pp. 9-21, (1997).
Clauw D.J. et al., Neuroimmunomodul tion,"Chronic Pain and Fatigue Syndromes: Overlapping Clinical and Neuroendocrine Features and Potential Pathogenic Mechanisms", vol. 4, No. 3, pp. 134-153, (1997).
Russell I.J. et al., the American Journal of the Medical Sciences, "Advances in Fibromyalgia: Possible Role for Central Neurochemicals", vol. 315, No. 6, pp. 377-384, (1998).
Russell I. J., Journal of Musculoskeletal Pain, "Substance P and Fibromyalgia", vol. 6, No. 3, pp. 29-35, (1998).
Russell I.J., Bulletin on the Rheumatic Diseases, Fibromyalgia Syndrome: Approaches to Management,vol. 45, No. 3, pp. 1-4, (1996).
Fukuda F. et al., Annals of Internal Medicine,"The Chronic Fatigue Syndrome: A Comprehensive Approach to Its Definition and Study", vol. 121, pp. 953-959, (1994).
Pillemer S.R. et al., Arthritis and Rheumatism,"The Neuroscience and Endocrinology of Fibromyalgia", vol. 40, No. 11, pp. 1928-1939 (1997).

(Continued)

*Primary Examiner*—Shaojia Anna Jiang
*Assistant Examiner*—Eric S Olson
(74) *Attorney, Agent, or Firm*—Daniel J Woods

(57) ABSTRACT

The invention relates to the pharmaceutical use of specific substance P antagonists, in particular 1-acylpiperidine substance P antagonists, especially N-benzoyl-2-benzyl-4-(aza-naphthoyl-amino)-piperidines, e.g. of formula

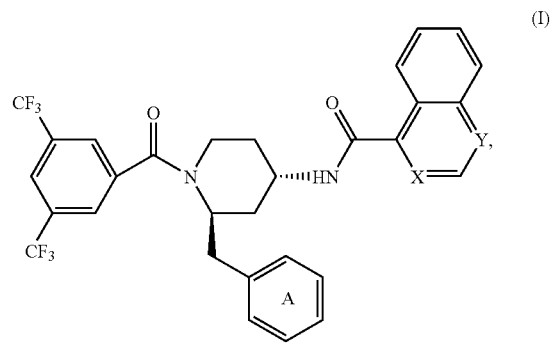

(I)

wherein X and Y are each independently of the other N and/or CH and the ring A is unsubstituted or mono- or poly-substituted by substituents selected from the group consisting of lower alkyl, lower alkoxy, halogen, nitro and trifluoromethyl; and pharmaceutically acceptable salts thereof for treatment of chronic fatigue syndrome (CFS) in the absence of serotonin agonist/selective serotonin reuptake inhibitory therapy, or for the treatment of fibromyalgia or associated functional symptoms.

6 Claims, No Drawings

OTHER PUBLICATIONS

Russell, I.J. et al., Arthritis and Rheumatism, "Elevated cerebrospinal fluid levels of substance P in patients with the fibromyalgia syndrome", vol. 37, No. 11, pp. 1593-1601,(1994).

Goldstein, Understanding Chronic Fatigue Syndrome, www.drjgoldstein.com, 1999.

Hardman et al., "Goodman & Gilman's The Pharmacological Basis of Therapeutics", $9^{th}$ ed, p. 51 and 57-58, (1996).

The Merck Manual of Diagnosis and Therapy, Seventeenth Edition, Beers, M. et al, editors, published by Merck Research laboratories, pp. 481-482 and 2481-2482, (1999).

Hill, R., "NK1 (Substance P) receptor antagonists—why are they not analgesic in humans?", Trends in Pharmacological Sciences, vol. 21, pp. 244-246, (2000).

Seward & Swain, Neurokinin receptor agonists, Exp. Opin. Ther. Patents, 9(5): 571-582 (1999).

Baby, et al., Substance P antagonists, J. Clin. Pharma. and Ther., 24: 461-469 (1999).

Bennett, Chronic widespread pain and the fibromyalgia construct, Oregon Health Sciences University.

Quartara & Maggi, The tachykinin NK1 receptor: ligands and mechanism of cellular activation, Neuropeptides, 31(6): 537-563 (1997).

Ladduwahetty et al., N-Heteroaryl-2-phenyl-3-benzyloxy-piperidines: a novel class of . . . NK1 antagonists, J. Med. Chem., 39: 2907-2914 (1996).

Fauchere, et al., The dipeptide NK-1 receptor antagonist S19752 . . . inhibitor of bronchioconstriction . . . guinea pig in vivo, Bioorgan. & Med. Chem. Let., 7(2): 203-208 (1997).

* cited by examiner

PHARMACEUTICAL USES

This is a continuation of application Ser. No. 11/715,805 filed on Mar. 8, 2007 which is a continuation of Ser. No. 10/947,967 filed on Sep. 23, 2004, which is a continuation of application Ser. No. 10/222,060, filed on Aug. 16, 2002, abandoned, which is a continuation of Ser. No. 09/792,801, filed on Feb. 23, 2001, abandoned, which is a continuation of International Application No. PCT/EP99/06215, filed on Aug. 24, 1999, the entire disclosures of which are hereby incorporated by reference.

This invention relates to substance P antagonists, in particular to 1-acylpiperidine substance P antagonists, and more specifically to new pharmaceuticals uses of such compounds.

Substance P antagonists and their pharmaceutical use for treatment of gastrointestinal disorders, inflammatory disorders, central nervous system disorders and pain are described in, for instance, WO 90/05525, WO 91/09844 and WO 91/18899. 1-acylpiperidines and more particularly N-benzoyl-2-benzyl-4-azanaphthoyl-amino piperidines and their activities as substance P antagonists are described in European patent EP 0532456 B and published European patent application EP 0739892 A and European patent EP 0707006 B respectively. The disclosures of EP 0532456 B, EP 0707006 B and EP 0739892 A are incorporated by reference in the teaching of the present application.

WO 96/24353 (Eli Lilly) describes a method for the treatment and prevention of a psychiatric disorder in a mammal which comprises administering to a mammal in need thereof an effective amount of a combination of a tachykinin receptor antagonist and either a serotonin agonist or a selective serotonin reuptake inhibitor. Chronic fatigue syndrome is listed amongst the numerous psychiatric disorders which are identified as candidates for treatment by this method.

Similarly WO 97/38692 (Eli Lilly) relates to a series of bisindoles which have activity both as tachykinin receptor antagonists and as serotonin agonists, and describes use of these bisindoles to treat migraine, pain or nociception, allergic rhinitis, the common cold, and a variety of psychiatric disorders including chronic fatigue syndrome amongst many others.

Surprisingly it has now been found that substance P antagonists, in particular 1-acylpiperidines and especially N-benzoyl-2-benzyl-4-(azanaphthoyl-amino)piperidines, and pharmaceutically acceptable salts thereof are particularly useful for treatment of chronic fatigue syndrome in the absence of serotonin agonist/selective serotonin reuptake inhibitory therapy.

Chronic fatigue disorders are a poorly defined clinical syndrome or combination of syndromes characterised by complaints of excessive fatigue and neurophysiological disturbances, often beginning after a viral infection. Attempts have been made to define diagnostic criteria for Chronic Fatigue Syndrome (CFS) but until recently the diagnosis has remained based on purely subjective criteria (Holmes et al. Annals of Internal Medicine 108: 387-389 (1988); Fukuda et al. Annals of Internal Medicine 121: 953-959 (1994)). In general, the fatigue is felt to be exacerbated following physical exertion, emotional stress, and/or viral illnesses. Lightheadedness, difficulty with thinking or concentrating, sleep disturbances, diffuse joint pain and tenderness, depression and weight fluctuations are often concurrent clinical features of chronic fatigue disorders. This general syndrome of chronic fatigue has also been designated CFS, neurasthenia, myalgic encephalomyelitis, fibromyalgia, post-viral syndrome, and chronic fatigue and immune dysfunction syndrome (CFIDS) (Price et al. Public Health Reports 107: 514-522 (1992)).

Considerable uncertainty exists concerning the etiological basis of this constellation of symptoms. There are few consistent objective clinical findings in the disorder except that it is more prevalent in females than in males (Price et al. Public Health Reports 107: 514-522 (1992); Bou-Hlaigah et al. JAMA 274: 961-967 (1995)).

Recently molecular genetic analysis has been applied to CFS (WO 98/37239—Glaxo) and it has been found that allelic variations within the arginine-vasopressin receptor-2 (AVPR2) gene are associated with variations in the clinical susceptibility to chronic fatigue disorders and this provides new methods for diagnosing CFS. These methods are described in WO 98/37239.

Substance P antagonists for use in the invention for treatment of CFS are 1-acylpiperidines and more particularly N-benzoyl-2-benzyl-4-azanaphthoyl-amino piperidines; for instance as described in EP 0532456 B, EP 0707006 B and EP 0739892A.

Surprisingly it has also now been found that 1-acylpiperidine substance P antagonists, especially N-benzoyl-2-benzyl-4-azanaphthoyl-amino)piperidines, and pharmaceutically acceptable salts thereof are particularly useful for treatment of fibromyalgia or associated functional symptoms of fibromyalgia.

Accordingly the present invention provides the use of a 1-acylpiperidine substance P antagonist or a pharmaceutically acceptable salt thereof in the manufacture of a medicament for treatment of CFS, or fibromyalgia or associated functional symptoms of fibromyalgia.

Fibromyalgia is a disease characterized by widespread muskuloskeletal pain and tenderness on palpation at so called tenderpoints. The disease is diagnosed according to criteria as defined by the American College of Rheumatology (ACR) [see Arthritis and Rheumatism, Vol. 33, No. 2, pages 160-172, 1990]. In addition to pain symptoms, in the majority of fibromyalgia patients a variety of functional symptoms such as headache, insomnia, irritable bowel syndrome, sicca symptoms, increased sweating, dizziness, tremor, dyspnoea, arrhythmias, paraesthesias, headache/migraine, fatigue, psychopathological disorders and others occur. Therefore, the medical approaches towards management of fibromyalgia should not exclusively aim at relief of pain symptoms but also aim at improvements in functional symptoms.

The present invention is to be understood as embracing the treatment of fibromyalgia as such, as well as pain and/or functional symptoms associated with fibromyalgia either individually or collectively, e.g. use of 1-acylpiperidine substance P antagonists for treatment, e.g. the alleviation or amelioration of pain or any of the above mentioned symptoms as components of fibromyalgia. In addition to pain relief in fibromyalgia the present invention in particular provides for the treatment of the following functional symptoms as associated with fibromyalgia: including headache, insomnia, irritable bowel syndrome, sicca symptoms, increased sweating, dizziness, tremor, dyspnoea, arrhythmias, paraesthesias, headache/migraine, fatigue and psychopathological disorders.

1-Acylpiperidine substance P antagonists are hereinafter referred to as Preferred Compounds of the Invention.

The Preferred Compounds of the Invention include in particular the 1-aclypiperidine substance P antagonists as described and claimed in EP 0532456B. The Preferred Compounds of the Invention are conveniently used as monotherapy for the treatment of CFS.

Particularly preferred Preferred Compounds of the Invention are the compounds of EP 0739892 A, e.g. the compounds: (2R,4S)—N-[1-(3,5-bisfluoromethyl-benzoyl)-2-(4-chlorobenzyl)-piperidin-4-yl]-4-oxo-4H-1-benzopyran-2-carboxamide; (2R,4S)—N-[1-(3,5-bisfluoromethyl-benzoyl)-2-benzyl-piperidin-4-yl]-4-oxo-4H-1-benzopyran-2-carboxamide, and (2R,4S)—N-[1-(3,5-bisfluoromethyl-benzoyl)-2-(4-chlorobenzyl)-piperidin-4-yl]-6-fluoro-4-oxo-4H-1-benzopyran-2-carboxamide, and pharmaceutically acceptable salts thereof; and especially the compounds of EP 0707006 B, i.e. of formula I

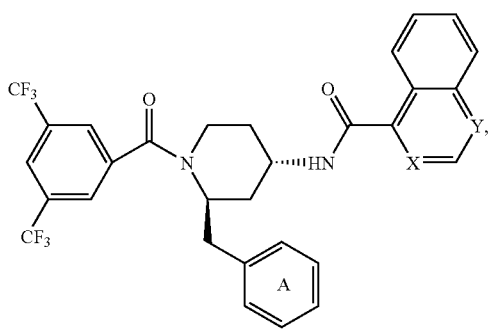

wherein X and Y are each independently of the other N and/or CH and the ring A is unsubstituted or mono- or poly-substituted by substituents selected from the group consisting of lower alkyl, lower alkoxy, halogen, nitro and trifluoromethyl; and pharmaceutically acceptable salts thereof, e.g. the compounds:
(2R,4S)—N-[1-(3,5-bis-trifluoromethyl-benzoyl)-2-benzyl-piperidin-4-yl]-quinoline-4-carboxamide;
(2R,4S)—N-[1-(3,5-bis-trifluoromethyl-benzoyl)-2-benzyl-piperidin-4-yl]-quinazoline-4-carboxamide;
(2R,4S)—N-[1-(3,5-bis-trifluoromethyl-benzoyl)-2-(4-chloro-benzyl)-piperidin-4-yl]-quinoline-4-carboxamide;
(2R,4S)—N-[1-(3,5-bis-trifluoromethyl-benzoyl)-2-(4-chloro-benzyl)-piperidinyl]-quinazoline-4-carboxamide;
(2R,4S)—N-[1-(3,5-bis-trifluoromethyl-benzoyl)-2-(4-chloro-benzyl)-piperidinyl]-isoquinoline-1 carboxamide;
(2R,4S)—N-[1-(3,5-bis-trifluoromethyl-benzoyl)-2-(4-nitro-benzyl)-piperidinyl]-quinazoline-4-carboxamide;
or in each case a salt thereof.

Suitable pharmaceutically acceptable salts, e.g. for oral administration, are described in EP 0707006B.

Preference is given to compounds of formula I wherein the ring A is substituted.

The invention relates especially to the use of compounds of formula IA

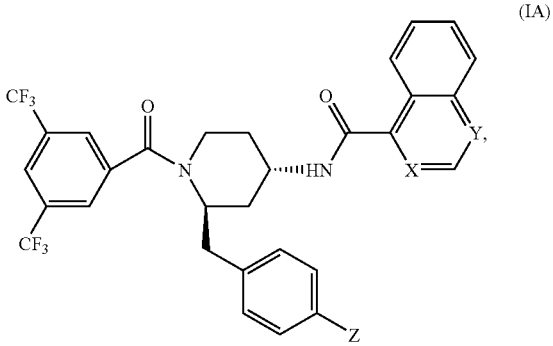

wherein X is CH or N and Y is N, and Z is hydrogen, halogen or nitro, and to the pharmaceutically acceptable salts thereof.

The invention relates more especially to use of compounds of formula IA wherein X is N or CH and Y is N, and Z is halogen, such as chlorine, and to the pharmaceutically acceptable salts thereof.

Most especially the invention relates to the use of the compound (2R,4S)—N-[1-(3,5-bistrifluoromethylbenzoyl)-2-(4-chlorobenzyl)-piperidin-4-yl-quinolin-4-carboxamide, and to the pharmaceutically acceptable salts thereof.

Unless otherwise defined, the general terms used hereinbefore and hereinafter have the meanings given in EP 0707006 B.

The usefulness of the Preferred Compounds of the Invention, for treatment of Chronic Fatigue Syndrome (CFS) is demonstrated in the following clinical study.

CFS Clinical Study

Patient Population

Patients with chronic fatigue syndrome according to the CDC (Centre for Disease Control) definition (G. P. Holmes et al.: A working case definition. Ann. intern. Med; 108 (1988), 387-389) are included in the trial. Other recognised definitions may be used to identify patients with chronic fatigue syndrome as appropriate. Both male and female patients are eligible, provided they are over 18 years of age and under 65 years of age. The main exclusion criteria comprise pregnant and lactating women; in addition patients suffering from other diseases that cause significant fatigue as well as patients who suffer from active infections are excluded. Other exclusion criteria comprise severe rheumatological diseases, severe neuropathies, clinically manifest endocrinopathies, psychiatric diseases (including depression), fibromyalgia, and severe cardial, renal and hepatic impairment.

The study is in the form of a prospective, randomized, double-blind, placebo-controlled, parallel-group study using different doses of a Preferred Compound of the Invention, (e.g. (2R,4S)—N-[1-(3,5-bistrifluoromethylbenzoyl)-2-(4-chlorobenzyl)-piperidinyl-quinolin-4-carboxamide).

Patients are randomly assigned to one of five study arms: placebo, 1 mg, 5 mg, 10 mg and 20 mg of test compound. (Preferably, for reliable evaluation of efficacy, each study arm includes 30 patients, giving a total sample size of 150 patients for the complete study.) The duration of treatment is four weeks. Before, on days 7, 14 and 21 and at the end of the treatment phase, a physical examination as well as assessment of fatigue and other symptoms are performed. Before study entry and at the end of the treatment blood tests are carried out. In order to document the daily intensity of fatigue, adverse events and concomitant medications, patients use a standardized diary and record daily the parameters mentioned. In addition, other symptoms as mentioned above, which are associated with CFS such as functional symptoms or cognitive impairment and myalgias are documented at start of treatment, and on days 7, 14, 21 and at the end of treatment. Adverse events are assessed during the active treatment period.

Regarding changes in fatigue, a visual analog scale is used. This analog scale is represented by a 100-mm-line with one end (=0) indicating "no fatigue" and the other end (=100) indicating "worst fatigue". Patients are asked to make a mark on the 100 mm scale which corresponds to their current fatigue intensity.

Other parameters which are evaluated include cognitive impairment (to be measured by visual analog scale [VAS]) and the assessment of myalgias. In the latter case a VAS is also used for evaluation; for instance, as described above for assessment of fatigue, in addition to use of a pain score. The pain score allows an assessment of different body regions and ranges from 0 to 120, measuring the pain intensity in a total of 24 body regions. The following rating scale is applied: 0=no pain, 1=mild pain, 2=moderate pain, 3=moderately severe pain, 4=severe pain, 5=most severe pain. The assessment of each body region is done by the patients themselves; the total score is calculated as the sum of the regional scores.

The following functional symptoms are evaluated in detail: cold hands/feet, sicca symptoms, increased sweating, dizziness, tremor, difficulties in falling asleep, difficulties in sleeping through, gastric problems, symptoms of irritable bowel syndrome, problems with swallowing, dyspnoea, arrythmias, paresthesias, painful micturation, headache/migraine, and morning stiffness. For each of the symptoms mentioned, patients are asked to rate the presence of the symptoms according to a score ranging from 0 to 3 (0=not present, 1=slightly present, 2=moderately present, 3=strongly present).

In addition to the documented effects during the active treatment phase, a follow-up of the patients is performed for six months in order to evaluate the duration of the clinical response (as defined by a 20% or higher reduction in any of the following symptoms: fatigue, myalgias, cognitive impairment; comparison of baseline vs end of treatment).

Up to now there has been no standard or effective treatment for chronic fatigue syndrome. Thus it is proposed that a Compound of the Invention is considered as effective in treatment of CFS if one or more doses of the Compound leads to a response rate at least 10% higher as compared to placebo, wherein the response rate is the clinical response rate as defined above. The usefulness of the Preferred Compounds of the Invention for treatment of fibromyalgia or associated functional symptoms is demonstrated in the following clinical study.

Fibromyalgia Clinical Study

The study is in the form of a prospective, randomized double-blind, placebo-controlled, parallel-group study using different doses of Compound of the Invention. Male and female patients (over 18 years) who meet the ACR (American College of Rheumatology) criteria for primary fibromyalgia are included in this trial. The main exclusion criteria include pregnant and lactating woman, patients suffering from other inflammatory rheumatological diseases (such as rheumatoid arthritis or collagenoses), severe neuropathies, clinically manifest endocrinopathies, bone diseases, severe cardial, renal or hepatic impairment and acute or chronic infections.

Patients are randomly assigned to one of five study arms, placebo, 1 mg, 10 mg, 20 mg and 40 mg of test compound. The duration of treatment is two weeks. Before, on day 7 and at the end of the treatment phase, a physical examination, pain assessment and blood testing are performed. In order to document daily the intensity of pain, adverse events and concomitant medications, patients use a standardized diary and record daily the parameters mentioned. In addition, changes in functional symptoms are documented at start of treatment, on day 7 and at the end of treatment. Adverse events are assessed during the active treatment period.

To evaluate pain, the pain score, a visual analogue scale and clinical examination of tenderpoints is used. The pain score ranges from 0 to 120, measuring the pain intensity in 24 body regions applied to the following rating scale: 0=no pain, 1=mild pain, 2=moderate pain, 3=moderately severe pain, 4=severe pain, 5=most ever pain. The assessment of each body region is done by the patients themselves; the total score is calculated as the sum of the regional scores.

The visual analogue scale is in the form of 10 mm-line oriented horizontally with one end=0, indicating "no pain" and the other end=100, indicating "worst pain". The patients are asked to place a mark corresponding to their perception of their present pain intensity.

In addition to the documented effects during the active treatment phase, a follow-up of the patients is performed for six months in order to evaluate the duration of the clinical response (as defined by a 35% or higher reduction in individual pain score/baseline versus end of treatment).

Amitryptilin, an antidepressant drug, is regarded an effective treatment in fibromyalgia and leads to response rates of about 20 to 30% of patients.

For use in accordance with the invention Preferred Compounds of the Invention most suitably are administered to human patients at a dose of about 1 to about 40 mg/kg per day. The Preferred Compounds of the Invention may be administered suitably in unit dosage form; for instance, in divided doses 1 to 5 times daily depending on the particular purpose of therapy, the phase of therapy and the like.

Suitable dosage form for use in accordance with the invention include forms for enteral, for example oral, or parenteral administration. Thus, tablets or gelatin capsules which have the active substance together with diluents, for example lactose, dextrose, sucrose, mannitol, sorbitol, cellulose and/or lubricants, for example diatomaceous earth, talc, stearic acid or salts thereof, such as magnesium or calcium stearate, and/or polyethylene glycol may be used. Tablets may likewise have binders, for example magnesium aluminium silicate, starches such as maize, wheat rice or arrowroot starch, gelatin, tragacanth, methylcellulose, sodium carboxymethylcellulose and/or polyvinylpyrrolidone and, if required, disintegrants, for example starches, agar, alginic acid or a salt thereof, for example sodium alginate and/or effervescent mixtures, or absorbents, dyes, flavourings and sweeteners. It is furthermore possible for the Compounds of the Invention to be used in the form of products which can be administered parenterally or of infusion solutions. Solutions of this type are preferably isotonic aqueous solutions or suspensions, it being possible to prepare the latter, for example in the case of lyophilized products which comprise the active substance alone or together with an excipient, for example mannitol, before use. The pharmaceutical products can be sterilized and/or comprise ancillary substances, for example preservatives, stabilizers, wetting agents and/or emulsifiers, solubilizers, salts to control the osmotic pressure and/or buffers. The present pharmaceutical products which, if required, may comprise further pharmacologically active substance, are produced in an manner known per se, for example by conventional mixing, granulating, coating, dissolving or lyophilizing processes, and comprise from about 0.1% to 100%, in particular from about 1% to about 50%, lyophilizates up to about 100%, of the active substance.

Preferred pharmaceutical compositions comprising the Preferred Compounds of the invention are spontaneously dispersible pharmaceutical compositions, for instance as described in bur copending International patent application PCT/EP 99/03623. The disclosure of International patent application PCT/EP 99/03623 is incorporated by reference in the teaching of the present application. Specific preferred compositions are described in Examples 4 to 11.

Substance P antagonists are known in the art and may be prepared or obtained by methods known in the art; for instance, as described in EP 0532456B, EP 0707006 B and EP 0739892 A for Preferred Compounds of the Invention.

EXAMPLES

Example 1

Tablets, each comprising e.g. 50 mg of (2R,4S)—N-[1-(3,5-bistrifluoromethylbenzoyl)-2-(4-chlorobenzyl)-piperidin-4-yl-quinolin-4-carboxamide or a pharmaceutically acceptable salt, for example the dihydrochloride, thereof, can be prepared as follows:

| Composition (10000 tablets) | |
|---|---|
| active ingredient | 500.0 g |
| lactose | 500.0 g |
| potato starch | 352.0 g |
| gelatin | 8.0 g |
| talc | 60.0 g |
| magnesium stearate | 10.0 g |
| silicon dioxide (highly dispersed) | 20.0 g |
| ethanol | q.s. |

The active ingredient is mixed with the lactose and 292 g of potato starch and the mixture is moistened with an ethanolic solution of the gelatin and granulated through a sieve. After drying, the remainder of the potato starch, the magnesium stearate, the talc and the silicon dioxide are mixed in and the mixture is compressed to form tablets, each weighing 145.0 mg and comprising 50.0 mg of active ingredient; the tablets may, if desired, be provided with breaking notches for finer adaptation of the dose.

Example 2

Film-coated tablet, each comprising 100 mg of (2R,4S)—N-[1-(3,5-bistrifluoromethylbenzoyl)-2-(4-chlorobenzyl)-piperidin-4-yl-quinolin-4-carboxamide or a pharmaceutically acceptable salt, for example the dihydrochloride, thereof, can be prepared as follows:

| Composition (for 1000 film-coated tablets) | |
|---|---|
| active ingredient | 100.0 g |
| lactose | 100.0 g |
| corn starch | 70.0 g |
| talc | 60.0 g |
| calcium stearate | 1.5 g |
| hydroxypropylmethylcellulose | 2.36 g |
| shellac | 0.64 g |
| water | q.s |
| methylene chloride | q.s. |

The active ingredient, the lactose and 40 g of the corn starch are mixed and moistened with a paste prepared from 15 g of corn starch and water (with heating) and granulated. The granules are dried, the remainder of the corn starch, the talcum and the calcium stearate are added and mixed with the granules. The mixture is compressed to form tablets (weight: 280 mg) which are then film-coated with a solution of the hydroxypropylmethylcellulose and the shellac in methylene chloride; final weight of the film-coated tablet: 283 mg.

Example 3

Hard gelatin capsules, comprising 100 mg of active ingredient, for example (2R,4S)—N-[1-(3,5-bistrifluoromethylbenzoyl)-2-(4-chlorobenzyl)-piperidin-4-yl-quinolin-4-carboxamide or a pharmaceutically acceptable salt, for example the dihydrochloride, thereof, can be prepared, for example, as follows:

| Composition (for 1000 capsules) | |
|---|---|
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve of 0.2 mm mesh size. The two components are intimately mixed. Then first the lactose is added through a sieve of 0.6 mm mesh size and then the microcrystalline cellulose is added through a sieve of 0.9 mm mesh size. The mixture is then intimately mixed again for 10 minutes. Finally the magnesium stearate is added through a sieve of 0.8 mm mesh size. After mixing for a further 3 minutes, size 0 hard gelatin capsules are each filled with 390 mg of the resulting formulation. Soft gelatin capsules may be prepared using similar ingredients and procedures.

Preferred compositions are described by way of illustration onyl in the following Examples, 4 to 11. Unless otherwise indicated, components are shown in % by weight based on each composition. Mean particle sizes (diameters) are measured at 20° C. using a Malvern Zetasizer.

All ingredients of the Examples are given in mg/capsule.

|  | Ex 4a[1] | Ex 4b[1] | Ex 5[2] | Ex 6[2] | Ex 7[2] | Ex 8[2] | Ex 9[2] | Ex 10[2] | Ex 11[2] |
|---|---|---|---|---|---|---|---|---|---|
| Active Agent | | | | | | | | | |
| Compound A | 5.0 | 1.0 | 1.0 | 5.0 | 1.0 | 10.0 | 7.5 | 17.0 | 14.0 |
| 1) Surfactant | | | | | | | | | |
| Cremophor RH 40 | 232.0 | 232.0 | 269.0 | | | 225.0 | 180.0 | 200.0 | 200.0 |
| Tween 80 | | | | 269.0 | 269.0 | | | | |

-continued

| | Ex 4a[1] | Ex 4b[1] | Ex 5[2] | Ex 6[2] | Ex 7[2] | Ex 8[2] | Ex 9[2] | Ex 10[2] | Ex 11[2] |
|---|---|---|---|---|---|---|---|---|---|
| 2) Hydrophilic component | | | | | | | | | |
| Propylene carbonate | | | | | | | | 25.0 | 50.0 |
| Caprylic acid | | | | | | | | | 50.0 |
| Triethyl citrate | | | | | | | 45.0 | 50.0 | |
| Propylene glycol | 46.5 | 46.5 | | | 90.0 | 45.0 | | | |
| Polyethylene glycol 400 | | | 90.0 | 90.0 | | | | | |
| Dimethyl isosorbide | | | | | | | | 50.0 | |
| Labrafil 2125 | | | | 90.0 | 90.0 | | | | |
| Caprylic/capric acid glycerides (Capmul MCM) | | | | | | 170.0 | 218.5 | | |
| Propyleneglycol monocaprylate Miglyol 812 | | | | | | | | 133.0 | 136.0 |
| refined corn oil[3] | 185.0 | 185.0 | 90.0 | | | | | | |
| 4) Hydrophilic co-component | | | | | | | | | |
| Ethanol abs | 52.0 | 52.0 | 50.0 | 50.0 | 50.0 | 50.0 | 50.0 | 50.0 | 50.0 |
| Additive | | | | | | | | | |
| DL-alpha tocopherol | 0.5 | 0.5 | | | | | | | |
| TOTAL | 504.0 | 500.0 | 500.0 | 504.0 | 500.0 | 500.0 | 500.0 | 500.0 | 500.0 |
| mean particle size (nm) | 80-90 | 80-90 | 20-30 | 135-145 | 25-35 | — | — | — | — |

[1] Compound A is dissolved in (1) with stirring at room temperature and (2) and (3) are added to the obtained solution again with stirring. 0.5 ml portions of the obtained mixture are filled into size 1 hard gelatine capsules and sealed, e.g. using the Quali-Seal technique, or into soft gelatine capsules. In another embodiment of Examples 1a and 1b, Compound A is dispersed in a mixture of components 1), 2) and 3), and combined with component 4).
[2] The carrier medium is prepared by mixing the components one with another. Compound A is then dissolved in the carrier medium by stirring.
[3] Refined oil = "refined glycerol-transesterified corn oil", substantially glycerol free, as described in GB 2 257 359 and WO 94/09211.
No phase separation or precipitation is observed for any of the above compositions 1 to 8 which are clear for 4 hours.

The Preferred Compounds of the Invention are safe for use in humans. Thus (2R,4S)—N-[1-(3,5-bistrifluoromethylbenzoyl)-2-(4-chlorobenzyl)-piperidin-4-yl-quinolin-4-carboxamide is well tolerated in human at a dose of up to about 100 mg/kg or more, e.g. up to about 200 mg/kg.

On administration of Preferred Compounds of the Invention, in particular the compound (2R,4S)—N-[1-(3,5-bistrifluoromethylbenzoyl)-2-(4-chlorobenzyl)-piperidin-4-yl-quinolin-4-carboxamide, at doses as indicated above, e.g. at doses of 10 to 20 mg/day, a positive outcome is recorded with response rates for fibromyalgia treatment at least equivalent to or comparable with those achieved with Amitryptilin and for CFS treatment at least equivalent to a 20% reduction in the score for one or more symptoms of CFS as described above.

The invention claimed is:

1. A method of treating Chronic Fatigue Syndrome in the absence of serotonin agonist/selective serotonin reuptake inhibitory therapy, comprising administering to a patient in need thereof, a 1-acylpiperidine substance P antagonist, the 1-acylpiperidine substance P antagonist comprising a compound of formula

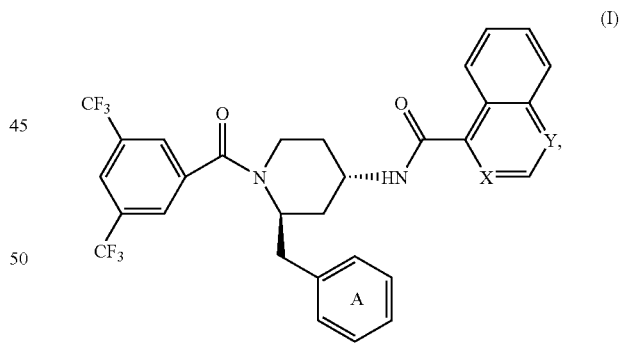

wherein X and Y are each independent of the other N and/or CH, and the ring A is unsubstituted or mono- or poly-substituted by substituents selected from the group consisting of lower alkyl, lower alkoxy, halogen, nitro and trifluoromethyl and for each compound, pharmaceutically-acceptable salts thereof.

2. The method of treatment according to claim 1, in which the 1-acylpiperidine compound is selected from the group consisting of (2R,4S)—N-[1-(3,5-bis-trifluoromethyl-benzoyl)-2-benzyl-piperidin-4-yl]-quinoline-4-carboxamide; (2R,4S)—N-[1-(3,5-bis-trifluoromethyl-benzoyl)-2-benzyl-piperidin-4-yl]-quinazoline-4-carboxamide; (2R,4S)—N-[1-

(3,5-bis-trifluoromethyl-benzoyl)-2-(4-chloro-benzyl)-piperidin-4-yl]-quinoline-4-carboxamide; (2R,4S)—N-[1-(3,5-bis-trifluoromethyl-benzoyl)-2-(4-chloro-benzyl)-piperidinyl]-quinazoline-4-carboxamide; (2R,4S)—N-[1-(3,5-bis-trifluoromethyl-benzoyl)-2-(4-chloro-benzyl)-piperidinyl]-isoquinoline-1-carboxamide; and (2R,4S)—N-[1-(3,5-bis-trifluoromethyl-benzoyl)-2-(4-nitro-benzyl)-piperidinyl]-quinazoline-4-carboxamide and for each compound, salts thereof.

3. A method of treating chronic fatigue syndrome in the absence of serotonin agonist/selective serotonin reuptake inhibitory therapy, comprising: administering to a patient in need thereof compound selected from the group consisting of (2R,4S)—N-[1-(3,5-bisfluoromethyl-benzoyl)-2-(4-chlorobenzyl)-piperidin-4-yl]-4-oxo-4H-1-benzopyran-2-carboxamide; (2R,4S)—N-[1-(3,5-bisfluoromethyl-benzoyl)-2-benzyl-piperidin-4-yl]-4-oxo-4H-1-benzopyran-2-carboxamide; end (2R,4S)—N-[1-(3,5-bisfluoromethyl-benzoyl)-2-(4-chlorobenzyl)-piperidin-4-yl]-6-fluoro-4-oxo-4H-1-benzopyran-2-carboxamide, and pharmaceutically-acceptable salts thereof.

4. The method of treatment according to claim 1, in which the 1-acylpiperidine compound is used as mono-therapy for the treatment of chronic fatigue syndrome.

5. The method of treatment according to claim 2, in which the 1-acylpiperidine compound is used as mono-therapy for the treatment of chronic fatigue syndrome.

6. The method of treatment according to claim 3, in which the compound is used as mono-therapy for the treatment of chronic fatigue syndrome.

\* \* \* \* \*